(12) United States Patent
Beller

(10) Patent No.: US 11,528,929 B2
(45) Date of Patent: Dec. 20, 2022

(54) COMPOSITION FOR TREATMENT OF OVERACTIVE BLADDER

(71) Applicant: Michael Beller, Jamaica, NY (US)

(72) Inventor: Michael Beller, Jamaica, NY (US)

( * ) Notice: Subject to any disclaimer, the term of this patent is extended or adjusted under 35 U.S.C. 154(b) by 45 days.

(21) Appl. No.: 17/038,633

(22) Filed: Nov. 9, 2020

(65) Prior Publication Data

US 2021/0051989 A1 Feb. 25, 2021

Related U.S. Application Data

(63) Continuation-in-part of application No. 16/293,195, filed on Mar. 5, 2019, now Pat. No. 10,792,320.

(51) Int. Cl.
| | |
|---|---|
| *A61K 36/42* | (2006.01) |
| *A23L 33/105* | (2016.01) |
| *A23L 33/155* | (2016.01) |
| *A23L 33/22* | (2016.01) |
| *A23L 33/00* | (2016.01) |
| *A23L 33/18* | (2016.01) |

(52) U.S. Cl.
CPC .......... *A23L 33/105* (2016.08); *A23L 33/155* (2016.08); *A23L 33/18* (2016.08); *A23L 33/22* (2016.08); *A23L 33/30* (2016.08)

(58) Field of Classification Search
None
See application file for complete search history.

(56) References Cited

U.S. PATENT DOCUMENTS

| | | | | |
|---|---|---|---|---|
| 10,792,320 B2 * | 10/2020 | Beller | ............... | A61K 31/198 |
| 2013/0115329 A1 * | 5/2013 | Savant | ............... | A23L 29/30 |
| | | | | 426/2 |
| 2013/0261183 A1 * | 10/2013 | Bhagat | ............... | G16H 70/60 |
| | | | | 514/560 |
| 2019/0110514 A1 * | 4/2019 | Vetter | ............... | A23L 33/29 |
| 2019/0374552 A1 * | 12/2019 | Hoag | ............... | A61K 31/351 |
| 2020/0221753 A1 * | 7/2020 | Qvyjt | ............... | G06Q 30/0601 |

* cited by examiner

*Primary Examiner* — Ralph J Gitomer

(57) ABSTRACT

A nutritional supplement composition for treatment of bladder disorders, in particular, overactive bladder (OAB) includes therapeutically effective amounts of pumpkin seed extract, nitric oxide precursor, vitamin D3, prebiotic fiber, preservative, and stabilizer.

5 Claims, 1 Drawing Sheet

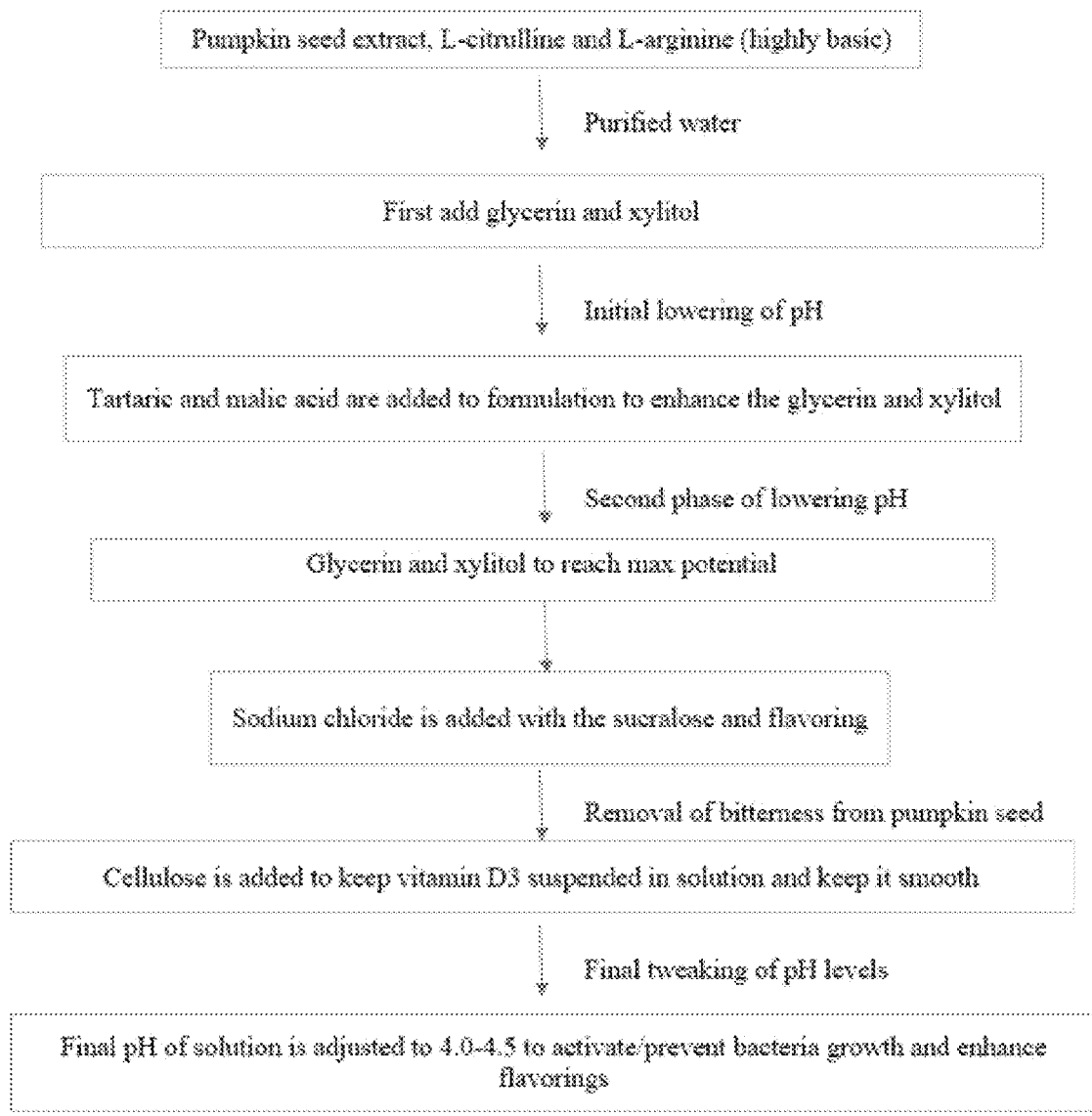

COMPOSITION FOR TREATMENT OF OVERACTIVE BLADDER

CROSS-REFERENCE TO RELATED APPLICATIONS

The present application is a continuation-in-part Application of U.S. application Ser. No. 16/293,195 filed on Mar. 5, 2019, now allowed as U.S. Pat. No. 10,792,320, the entire contents of which being hereby incorporated by reference.

FIELD OF THE INVENTION

The present disclosure relates to nutritional supplements and more particularly to a nutritional supplement composition for treatment of bladder disorders, in particular, overactive bladder (OAB).

BACKGROUND OF THE INVENTION

Overactive bladder may be due to a number of factors. One such cause of overactive bladder is benign prostate hyperplasia (BPH), a common condition in aging men. The bladder dysfunction symptoms are related to the effect of the enlarged prostate on the urethra which creates a partial urethral obstruction. Other causes of outlet obstruction that results in bladder dysfunction include but are not limited to cancer, sclerosis or fibrosis of the bladder neck, urethral structure disease, urethral valves, and smooth and striated sphincter dyssynergia. An overactive bladder might also occur as a result of neurological damage due to disorders including but not limited to stroke, Parkinson's disease, diabetes, multiple sclerosis, peripheral neuropathy, or spinal cord lesions.

When the bladder is functioning normally, the muscles in the bladder wall remain relaxed, allowing the bladder to expand and store urine. During urination, the muscles contract, the bladder sphincters open, and urine is voluntarily released. People who have overactive bladder syndrome (OAB) experience "urgency," which is the sudden, strong urge to urinate. If the urge cannot be suppressed due the over activity and weakening of the detrusor muscle, involuntary leakage of urine results. Other symptoms of OAB include the need to urinate many times during the day (urinary frequency) and at night (nocturia).

There are many nutritional supplements on the market that purport to promote general health. These supplements typically take the form of tablets, capsules, or powders that are combined with meals as part of a healthy diet regimen.

Apart from nutritional supplements that are designed to promote general health, there are also dietary products on the market directed at bladder control. Other products in the form of pills or tablets do not have the effect of absorbing as much into the patient body compared with a pure liquid. While these products may suppress incontinence, the lack of variance in ingredients fails to create a continuous homeostasis process that creates uniformity while the body is in constant flux. These products may be effective for a short time by absorbing liquid content in the bladder, creating a less frequent urge to urinate, but ultimately users experience return of their urogenital disorder symptoms.

Accordingly, there remains a need for a natural composition specifically formulated for treating bladder dysfunction without the use of pharmaceutical drugs, which require a prescription and accord high incidences of side effects without effectively addressing the underlying bladder disorder or attacking the issue through different mechanisms of action to achieve the desired results.

SUMMARY OF THE INVENTION

A nutritional supplement composition combining amino acids, vitamins, plant extracts, and essential nutrients along with gentle digestive enzymes is disclosed. This over the counter dietary supplement is made up various types of natural ingredients and when combined, supports healthy bladder control and overall health. The supplement provides a completely natural bladder control aid that suppresses urgency, frequency, and leakage. Other essential nutrients may be further included.

The combination of the aforementioned specific components yields a composition directed particularly at bladder control, relaxation, support and strengthening. This composition contains components that were not previously known or expected to additively to increase or enhance the composition's effectiveness.

In one aspect thereof, a nutritional supplement for inhibiting incontinence includes a combination of vitamin D3, prebiotic fiber, pumpkin seed extract, and nitric oxide precursor. In a particular aspect thereof, a nutritional supplement for inhibiting incontinence includes a combination of vitamin D3, prebiotic fiber, pumpkin seed extract, and L-citrulline.

In one embodiment, the supplement includes in a single serving size of 30 ml including active ingredients comprised of about 550 mg of pumpkin seed extract, 500 mg L-citrulline, 1500 mg prebiotic fiber and 1500 IU of vitamin D3. In addition, this formulation strengthens the pelvic floor and sphincters by inhibiting key enzymes (aromatase) which helps conserve testosterone and builds muscles.

The "Combination" of ingredients, the "Dosage" of the ingredients, the "Preparation" of the ingredients and the "Inactive agents" (Preservatives and stabilizers) at the correct pH levels, create the uniqueness of the present compositions, which would not be found in this combination in nature. Individual ingredients might separately be found in nature but would not be joined together at the specific unit dosage range in a liquid form to aid in a treatment for OAB symptoms. The pumpkin seed in embodiments of the present formulation has been modified to a specific dose of 500 mg and has been verified and proven to show a reduction in 5 Alfa reductase and decrease aromatase at this dosage. It has been shown that testosterone levels will increase, and dihydrotestosterones will decrease, thereby allowing a strengthening of the pelvic floor and sphincter muscles which will help improve overactive bladder in both men and women.

BRIEF DESCRIPTION OF THE DRAWING

The attached drawing FIGURE includes a flowchart representing sequential steps to for formulation of an embodiment of the present invention that is stable and exhibits an appropriate pH.

DETAILED DESCRIPTION OF THE INVENTION

The amounts of vitamin D3, pumpkin seed extract, L-citrulline, and prebiotic inulin may be varied within any suitable range to provide the desired effect.

The composition may be in any convenient nutritional supplement form.

The administration routes of the composition alternatively include enteral, e.g., oral or rectal, parental, or transdermal patch or extended/sustained release.

In making capsules, tablets, soft gels, patches, and liquid formulations, it is well known in the art that other inactive ingredients are necessary to make it palatable and to provide stability. Suitable binders, lubricant and other inactive components would be incorporated into the formulation. In addition, flavoring, preservatives, flow enhancers, filling aids and other agents may be also be desired.

It is to be appreciated that other suitable forms, such as powder or liquid, prepared in conventional manners, with or without food stuffs or inert carriers, are also contemplated.

Alternatively, a composition of the present disclosure can be rendered in a liquid form, suitable for patients that are unable to swallow a solid pill.

The contribution of each of the individual components is described as follows.

Pumpkin seed extract that is water-soluble exerts anabolic (tissue-building) effect on the pelvic floor muscles via several mechanisms. First, by inhibiting the aromatase enzyme, it may make more testosterone available to strengthen the pelvic muscles. Secondly, this water-soluble pumpkin seed fraction binds to the androgen receptor on pelvic muscle cells, thus inducing a strengthening effect. A preferred pumpkin seed product is EFLA@940—HYPERPURE manufactured by Frutarom, 521 West 57$^{th}$ Street, New York, N.Y. 10019. The pumpkin seed extract may be present preferably in a dose range of 100 mg-1,000 mg per day.

The processing of pumpkin seeds is extremely important, so that the clinical structure of the pumpkin seed is not denatured, thereby losing potency. There are different end products of pumpkin seed—pumpkin seed oil and pumpkin seed that has been defatted, making it water-soluble. In addition, there are different pumpkin seeds strains from different regions of the planet. Pumpkin seed oil is a viscous dark green to dark red oil that has a good source of polyunsaturated fatty acids, such as myristic acid/palmitic acid/steric acid/oleic acid/linolenic acid/arachidic acid, etc.

The pumpkin seed used in embodiments of the present invention is preferably an extract manufactured from defatted pumpkin seed of *Cucurbita pepo* L. ssp. *Pepo* var. *styriaca* from Austria. Extraction of the pumpkin seed to obtain a preferred pure product has multiple steps, and such product is not found in nature in this end state. Water/ethanol provides for a process of decontamination to increase stability, purity, and solubility, with no rancidity.

The manufacturing process ensures that each batch is checked for contaminants, heavy metals, pesticides, mycotoxins, and dioxins.

Specific Manufacturing Process of Pumpkin Seed

In the manufacture of embodiments of the present invention, a carrier is needed to help disperse the pumpkin seed extract so that it can be mixed into the rest of the formulation. A preferred carrier used was Maltodextrin in a range of 25%-27%. The extraction solvent used was ethanol and H2O in a ratio of 60:40 W/W to aid in the removal of the fatty substances of the pumpkin, making it lipid-free and available to be incorporated into a powder form and convertible into a liquid form that stays in suspension. No irradiation is necessary, but short-term heating of precursors is affected. The pumpkin seed thus processed does not contain significant microbiological contaminants, and <0.5% M/M ethanol concentrate remains at the finished product.

The purified processed pumpkin seed may be sufficiently purified so as to contain no allergens from the list including: gluten, crustaceans, eggs, fish, peanuts, soybeans, milk/dairy products, celery, mustard, sesame seeds, sulfur dioxide, sulfites, mollusks, and lupins. The purified pumpkin seed is suitable for vegan/vegetarian/gluten-free diets and may be non-GMO.

The nitric oxide precursor may preferably be present in an amount of about 50 mg-10,000 mg. Particularly preferred nitric oxide precursor L-citrulline in the body acts as an arginine precursor, meaning it is used in the production of arginine because it is the end product from L-citrulline being broken down in the kidneys. Its critical role in the human body is that of a nitric oxide precursor. Arginine may be used instead with similar results, as might other known nitric oxide precursors. The nitric oxide may comprise one or more known nitric oxide precursors.

Arginine and citrulline present in this formulation are in a correct ratio aiding in the production of nitric oxide (through the arginine pathway) and thereby allowing the bladder to relax and decrease urinary frequency. The arginine/citrulline increase production of nitrogen monoxide (NO) in the patient's body thereby allowing the bladder muscle to relax. This combination in this invention is not natural and is not found in nature in this ratio. The art of putting in L-arginine/L-citrulline is unique in that the citrulline helps create more arginine which in turn creates nitric oxide. Without the further addition of citrulline in the correct ratio to arginine, the additional nitric oxide would not be created thereby relaxing the bladder which will allow more urine to be stored.

Prebiotic fiber is a soluble carbohydrate fiber, one of three types of dietary fiber, including soluble, insoluble, and resistant starch. For a carbohydrate to have soluble fiber properties it must dissolve in water to form a gelatinous material. In the present disclosure, inulin is a preferred prebiotic fiber. Other prebiotic fibers include fructooligosaccharides, polydextrose, arabinogalactan, lactitol, transgalactooligosaccharides (TOS), isomaltooligosaccharides (IMO), xylooligosaccharides (XOS), alpha-glucooligosaccharides, soybean oligosaccharides, arabinoxylan-oligosaccharide. The prebiotic fiber may comprise one or more prebiotic fibers.

The solubility of prebiotic inulin is considered to be even higher than many other types of prebiotic fibers, meaning it absorbs water more easily than other carbohydrates and in conjunction with pepsin already in the human stomach helps form stool that can easily be passed through a digestive tract. Due to its chemical composition, when prebiotic inulin is mixed with liquid it forms a creamy gel. It is hypothesized by the present inventor that this form results in reduced pressure and tension being placed on the bladder, which is one direct connection with bladder leakage. In effect, the inclusion of prebiotic inulin dramatically increases the effectiveness of its co-components. Prebiotic inulin is preferably contained in a dose amount of about 500 mg to 15,000 mg per day.

Vitamins are vital elements to obtain a proper muscle function. The vitamin D family in particular helps the muscle and skeletal system in many ways. For example, vitamin D can regenerate muscles tissue, which increase functioning all over the body. Vitamin D plays a role in cosmetic care by promoting healthy skin, which is one of the areas that are body can absorb it from. Of particular use in the present composition is vitamin D3.

There are vitamin D receptors in the detrusor wall of the bladder and urethra. These receptors require vitamin D3 for muscle strengthening and improved bladder and urethra support. Muscle control and strength are vital for the voluntary control of the urethral sphincter and pelvic floor muscles and likely a significant factor in achieving continence. Vitamin D3 is preferably present in an amount of about 300 IU-10,000 IU daily.

Vitamin D3 is mixed into these other ingredients (pumpkin seeds/L-arginine/L-citrulline) etc., thus increasing efficacy of holding urine by improving bladder and urethra strength. Vitamin D3 attaches to the detrusor wall and promotes strength for the bladder and sphincter.

The composition according to one embodiment of the presently disclosed nutritional supplement exhibits maximum results in bladder control and strengthening. The effect of the components of the present disclosure produces synergistic results that were heretofore unachievable with prior bladder control supplements. This is because the prior supplements used only one component to address one area (e.g., pelvic strengthening) and did not consider how to maximize results or how treatment of the one area would affect other areas (e.g., well-being of intestinal health). The composition of the present disclosure, on the other hand, views bladder control, muscle relaxing, improved colonic motility, pelvic strengthening, and overall health/well-being as a complete package and recognizes that changes in one area affect other areas. The synergistic effect of the present composition is based on the presently described dosing and proportions, and the net effect is greater than any additive effect that might have been expected based on the known effect of the individual components.

Thus, the above composition describes an embodiment of the composition of the presently disclosed nutritional supplement that increases the muscle strength and other enzymes and other agents necessary to metabolize and utilize the inherent biological formalities of the body to solve multiple problems of the bladder. Combining the above components with essential vitamins, amino acids and in establishing a proper regulation of the digestive system, the composition of the presently disclosed nutritional supplement enhances the muscle strengthening of the bladder process in continuous and regulated manner.

Oral dosing is a preferred method due to 25 percent of Americans have difficulty in swallowing tablets, capsules, or pills. A "specific unit dosage range" in an oral form will allow the body to have immediate absorption and eliminate a first pass effect thereby reaching the targeted areas at an enhanced rate. The active ingredients do not have to be broken down before absorption which could possibly reduce the concentration of the active ingredients upon reaching its site of action.

A preservative such as, preferably, potassium sorbate is used in the invention (liquid form) to prevent mold, fungi, and yeast. In addition, it is highly soluble and can be used in the preferred pH range without concern that it will break down.

In addition to potassium sorbate, the inventor has also included malic acid and tartaric acid as pH adjusters. These agents will decrease the pH of the all-natural, highly basic active ingredients pumpkin seed extract, L-citrulline and L-arginine, and inhibit growth of yeast and some bacteria in the liquid formulation without harsh chemicals. Other organic acid preservatives would include, but not limited to, citric, sorbic, succinic, benzoic, lactic, and propionic acids. Other preservatives would include, but are not limited to, antioxidants that inhibit oxidation: sulfites, including sodium sulfite, sodium bisulfite, sodium metabisulfite, potassium bisulfite and potassium metabisulfite, vitamin E (tocopherol), vitamin C (ascorbic acid), butylated hydroxyanisole (BHA), and butylated hydroxytoluene (BHT).

Stabilizers are substances that make it possible to maintain the physico-chemical state of foodstuff, stabilizers include substances which enable the maintenance of a homogenous dispersion of two or more immiscible substances in a foodstuff and include also substances that stabilize, retain, or intensify an existing color of a foodstuff, and are preferably included in embodiments of the present invention.

A preferred stabilizer is cellulose gum, also known as sodium carboxymethyl cellulose or CMC, which is a natural water-soluble gum, polysaccharide found in plants.

Cellulose gum not only improves the storage time of vitamin D3, but it keeps it in suspension without separation. In addition, cellulose gum improves the mouthfeel, body, and texture of the compositions, and allows uniform dispersal of ingredients.

In addition, stabilizers may be added to cellulose gum. Preferred stabilizers that could be used with or alongside of cellulose gum include: polyglycerol polyricinoleate (PGPR), ammonium phosphatide (AMP), mono and diglycerides, carob (locust bean gum), agar-agar carrageenan, pectin or calcium chloride, lecithin, alginates (from seaweed), cellulose derivatives (from plants), alginic acid, gelatin, guar gum, gum arabic (acacia), ghatti gum, potassium alginate, karaya gum, tragacanth gum, and xanthan gum. Most of these can be modified from their original form.

It should be understood that detailed description herein is to be regarded in an illustrative rather than a restrictive manner and is not intended to be limiting to the particular forms and examples disclosed. On the contrary, further modifications, changes, rearrangements, substitutions, alternatives, and embodiments may be apparent to those of ordinary skill in the art, without departing from the spirit and scope hereof, as defined by the following claims. Thus, it is intended that the following claims be interpreted to embrace all such further modifications, changes, rearrangements, substitutions, alternatives, and embodiments.

The difficulty of this formulation lies in the ability to have a stable, uniform, and consistent end composition in the acidic range due to the nature of ingredients. The active ingredients are at all ends of the pH spectrum. Each ingredient needs to be incorporated in stages, with the pH being continually adjusted during the process.

There are two buffering systems that play an essential role in lowering the pH in order to provide us with a stable, efficacious, and pleasant tasting formula. The first buffering system includes glycerin and xylitol to initially lower the pH. To enhance the effect of these agents, tartaric and malic acid are added in this sequence, thus enabling the glycerin and xylitol to reach their maximum potential in stabilizing the pH. Other buffers would include, but not limited to, sodium phosphate, citric acid, acetic acid, aspartic acid and glutamic acid.

In the scope of production of the composition, the pH and acid levels will need to be adjusted for the following reasons:
 1. Initial pH too high
 2. End product needs to be acidic
 3. The flavoring system must remain acidic.

Initial ingredients are highly basic, including pumpkin seed extract, L-citrulline, and L-arginine. These ingredients need to be systematically acidified without losing their stability. In addition, vitamin D3 presents a unique problem because it will not stay in solution due to the fat content. The flavoring system presents a challenge because it must also remain in the acidic range in order for it to retain its flavor.

The addition of both malic acid and tartaric acid will affect the flavoring system as well as the overall total acidity (TA). To further complicate things, the addition of water may alter the pH.

In order for acid reduction to take place, the isoelectric point (dissociation point) must be considered, where the pH is at 50% bound and 50% in free form. The isoelectric pH is different for each acid, malic acid is 3.41 and tartaric acid is 2.96. For acid reduction to occur, it is essential for the isoelectric pH to be attained.

Ingredients in the formulation need to be incorporated in a systematic fashion to reduce and maintain the proper pH levels. The proper formulation is needed to meet the qualifications for consistent potency, stability, maintain palatability, and preventing growth of bacteria, yeast, and mold. In the art of formulation, one ingredient is specifically added to another to complement a previous ingredient allowing it to achieve its full function and create a lattice or building block effect. The sequential steps indicated on the drawing FIGURE need to be followed for the formulation to be stable and maintain the correct pH. Without proper order of introduction of each specific ingredient, there could be precipitation, and the pH would not be at the optimal level thus creating an unstable product.

I claim:

1. An acidic nutritional supplement composition effective for the treatment of overactive bladder (OAB), comprising therapeutically effective amounts of pumpkin seed extract,
   nitric oxide precursor,
   vitamin D3,
   prebiotic fiber,
   a preservative, and
   a stabilizer;
   wherein the preservative is at least one selected from the group consisting of potassium sorbate, malic acid, tartaric acid, citric acid, sorbic acid, succinic acid, benzoic acid, lactic acid, propionic acid, sodium sulfite, sodium bisulfite, sodium metabisulfite, potassium bisulfite, potassium metabisulfite, vitamin E (tocopherol), vitamin C (ascorbic acid), butylated hydroxyanisole (BHA), butylated hydroxytoluene (BHT), disodium ethylenediaminetetraacetic acid (EDTA), and polyphosphates: wherein the preservative is sufficient to decrease the pH of the nutritional supplement composition to 4.0-4.5 to inhibit bacteria growth; and
   wherein the stabilizer is
   cellulose gum, and
   optionally, at least one selected from the group consisting of polyglycerol polyricinoleate (PGPR), ammonium phosphatide (AMP), mono and diglycerides, carob (locust bean gum), agar-agar carrageenan, pectin, calcium chloride, lecithin, alginates (from seaweed), alginic acid, gelatin, guar gum, gum arabic (acacia), ghatti gum, potassium alginate, karaya gum, tragacanth gum, and xanthan gum;
   wherein the following amounts are contained in a daily administered unit dose:
   pumpkin seed extract 100 mg-1,000 mg,
   nitric oxide precursor 50 mg-10,000 mg,
   vitamin D3 300 IU-10,000 IU, and
   prebiotic fiber 500 mg-15,000 mg.

2. The nutritional supplement composition of claim 1, wherein the nitric oxide precursor is L-citrulline.

3. The nutritional supplement composition of claim 1, wherein the prebiotic fiber is inulin.

4. The nutritional supplement composition of claim 2, wherein the prebiotic fiber is inulin.

5. The nutritional supplement composition of claim 1, further comprising L-arginine.

* * * * *